United States Patent [19]

Schaub et al.

[11] 4,025,641
[45] May 24, 1977

[54] POLYETHER SUBSTITUTED 3,4-METHYLENEDIOXYBENZENES

[75] Inventors: Fritz Schaub, Basel; Hans-Peter Schelling, Oberwil, both of Switzerland

[73] Assignee: Sandoz Ltd., Basel, Switzerland

[22] Filed: May 5, 1975

[21] Appl. No.: 574,438

Related U.S. Application Data

[63] Continuation of Ser. No. 370,763, June 18, 1973, abandoned.

[30] Foreign Application Priority Data

June 23, 1972 Switzerland .................. 9520/72

[52] U.S. Cl. .................. 424/282; 260/340.5; 260/559 R; 260/609 R; 260/611 A; 260/611 B; 260/614 R; 260/615 B
[51] Int. Cl.² .................. A61K 31/36
[58] Field of Search .............. 260/340.5; 424/282

[56] References Cited

UNITED STATES PATENTS

| | | | |
|---|---|---|---|
| 2,764,517 | 9/1956 | Beroza | 260/340.5 R |
| 2,920,993 | 1/1960 | Fairchild | 424/282 |
| 3,035,063 | 5/1962 | Hedenburg | 260/340.5 R |
| 3,070,607 | 12/1962 | Barthel et al. | 260/340.5 R |
| 3,117,135 | 1/1964 | Hedenburg | 260/340.5 R |
| 3,770,774 | 11/1973 | Jenkins | 260/340.5 R |

*Primary Examiner*—Ethel G. Love
*Attorney, Agent, or Firm*—Gerald D. Sharkin; Richard E. Vila

[57] ABSTRACT

The present invention concerns novel aromatic long chain alkyl ethers and thioethers of the formula,

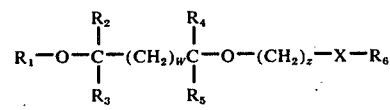

wherein
$R_1$ is a hydrocarbon group,
$R_2$, $R_3$, $R_4$ and $R_5$, are each hydrogen or alkyl,
$w$ and $z$ are integers,
X is an ether or thioether bridge, and
$R_6$ is an aromatic radical.

The compounds are useful as insecticides and acaricides.

13 Claims, No Drawings

POLYETHER SUBSTITUTED 3,4-METHYLENEDIOXYBENZENES

This is a continuation of application Ser. No. 370,763 filed June 18, 1973, now abandoned.

The present invention relates to ethers and thioethers and more specifically to aromatic long chain alkyl ethers and thioethers which possess insecticidal and acaricidal properties.

The present invention provides compounds of formula I,

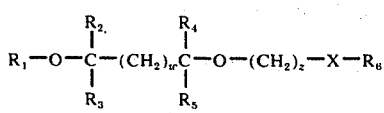

wherein
$R_1$ is alkyl of 1 to 9 carbon atoms, alkenyl of 3 to 9 carbon atoms, alkynyl of 3 to 9 carbon atoms, cycloalkyl of 5 to 7 ring carbon atoms, or cycloalkyl of 5 to 7 ring carbon atoms substituted by alkyl of 1 to 4 carbon atoms, $R_2$, $R_3$, $R_4$ and $R_5$, are each, independently, hydrogen or alkyl of 1 to 4 carbon atoms, $w$ is an integer 2 to 4, $z$ is an integer 2 to 6

X is oxygen, sulphur, a group —OCH$_2$— or —SCH$_2$—, and $R_6$ is an aromatic radical Ar$_1$

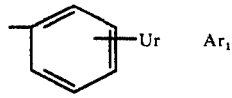

or an aromatic radical Ar$_2$

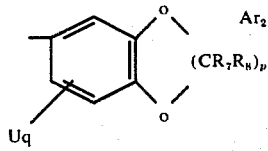

wherein
U is alkyl of 1 to 6 carbon atoms, alkenyl of 2 to 6 carbon atoms, alkoxy of 1 to 6 carbon atoms, alkenyloxy of 3 to 6 carbon atoms, formyl, alkylcarbonyl of 2 to 6 carbon atoms, carbamoyl mono- or di-substituted by alkyl of 1 to 6 carbon atoms, alkoxymethylene of 2 to 7 carbon atoms, alkylthio of 1 to 6 carbon atoms, cyano, nitro, chlorine, bromine or phenyl, $R_7$ and $R_8$ are each independently, hydrogen or alkyl of 1 to 6 carbon atoms, $r$ is an integer 1 to 2

$p$ is an integer 1 or 2 and $q$ is zero or an integer 1 or 2.

It is to be understood that when $r$ or $q$ are each the integer 2, then the two substituents U on the benzene ring may be the same or different.

Where any or all of $R_1$, $R_2$, $R_3$, $R_4$, $R_5$, $R_7$, $R_8$ or U are, or include, aliphatic hydrocarbon groups of more than 2 carbon atoms, then the aliphatic group may be straight or branched chain a primary or a secondary group, or when of more than 3 carbon atoms, then the aliphatic hydrocarbon group may be a tertiary group.

When $R_1$ is alkyl, this is preferably of 1 to 8 carbon atoms more preferably of 1 to 6 carbon atoms, particularly 3, 4, 5 or 6 carbon atoms, especially branched or secondary alkyl of 3, 4, 5 or 6 carbon atoms, more especially of 3, 4 or 5 carbon atoms, e.g. isopropyl, isobutyl and isopentyl.

When $R_1$ is alkenyl, this is preferably of 3 to 8 carbon atoms, more preferably of 3, 4, 5 or 6 carbon atoms, especially of 3, 4 or 5 carbon atoms e.g. allyl, but-3-ene-1-yl and pent-4-ene-1-yl, particularly allyl.

When $R_1$ is alkynyl, this is preferably of 3 to 8 carbon atoms, more preferably of 3, 4, 5 or 6 carbon atoms, especially of 3, 4 or 5 carbon atoms e.g. prop-2-yne-1-yl, but-3-yne-1-yl and pent-4-yne-1-yl.

When $R_1$ is or contains cycloalkyl this is preferably of 6 ring carbon atoms i.e. cyclohexyl. When $R_1$ is alkylcycloalkyl, this is preferably methylcyclohexyl, ethylcyclohexyl or n-propylcyclohexyl.

Preferably $R_1$ is alkyl of 1 to 9 carbon atoms.

When any of $R_2$, $R_3$, $R_4$ and $R_5$ is alkyl, this is preferably of 1, 2 or 3 carbon atoms, particularly methyl, ethyl or n-propyl especially methyl or ethyl, and particularly methyl.

Preferably, however, one of $R_2$ and $R_3$ and/or $R_4$ and $R_5$ is hydrogen.

Preferably the integers $w$ and $z$ are even numbers i.e. preferably $w$ is 2 or 4 and $z$ is 2, 4 or 6.

Preferably X is oxygen, —OCH$_2$— or —SCH$_2$— particularly oxygen or —OCH$_2$—.

When U is or includes an aliphatic hydrocarbon group, this is preferably of less than 6 carbon atoms, more preferably less than 5 carbon atoms, e.g. of 2, 3, or 4 carbon atoms. When U is alkyl this is preferably of 1 to 4 carbon atoms e.g. methyl, ethyl, n-propyl or n-butyl, particularly of 1 to 3 carbon atoms, more particularly methyl or ethyl. When U is alkoxy or alkylthio, this is preferably of 1, 2, 3 or 4 carbon atoms e.g. methoxy, ethoxy, n-propoxy or n-butoxy, or, methylthio, ethylthio, n-propylthio or n-butylthio, particularly methoxy or ethoxy, or, methylthio or ethylthio.

Preferably U is alkyl, alkoxy or alkylthio, especially alkyl or alkylthio.

When $R_7$ or $R_8$ is alkyl, this is preferably of 1, 2, 3, 4 or 5 carbon atoms, particularly methyl or ethyl.

Preferably one or both of $R_7$ and $R_8$ are hydrogen.

Preferably $r$ is the integer 1, $p$ is the integer 1 and $q$ is zero.

The present invention also provides a process for the production of compounds of formula I, which comprises a. condensing a compound of formula II, $$R_1-O-\underset{\underset{R_3}{|}}{\overset{\overset{R_2}{|}}{C}}-(CH_2)_w-\underset{\underset{R_5}{|}}{\overset{\overset{R_4}{|}}{C}}-O-(CH_2)_z-L \quad \text{II}$$

wherein
$R_1$, $R_2$, $R_3$, $R_4$, $R_5$, $w$ and $z$ are as defined above, and
L is chlorine, bromine or tosyl,
with a compound of formula III,

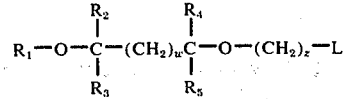

wherein X and $R_6$ are as defined above, and
M is hydrogen, sodium or potassium, in the presence of an acid binding agent when M of formula III is hydrogen, b. condensing a compound of formula IVa

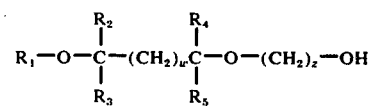   IVa wherein $R_1$, $R_2$, $R_3$, $R_4$, $R_5$, $w$ and $z$ are as defined above,
with a compound of formula IIIa HO—$R_6$   IIIa wherein $R_6$ is as defined above,
in the presence of dicyclohexyl carbodiimide as condensation agent, to obtain a compound of formula Ia,

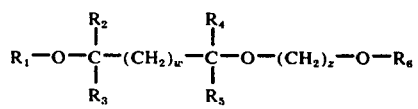   Ia wherein $R_1$, $R_2$, $R_3$, $R_4$, $R_5$, $R_6$, $w$ and $z$ are as defined above, c. condensing a compound of formula V,

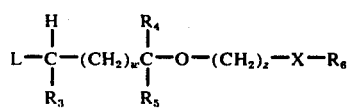   V wherein $R_3$, $R_4$, $R_5$, $R_6$, X, $w$, $z$ and L are as defined above,
with a compound of formula VI,

MOR$_1$   VI wherein M and $R_1$ are as defined above,
in the presence of an acid acceptor when M of formula VI is hydrogen, to produce a compound of formula Ib

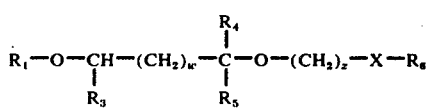   Ib wherein $R_1$, $R_3$, $R_4$, $R_5$, $R_6$, X, $w$ and $z$ are as defined above, d. condensing a compound of formula VII,

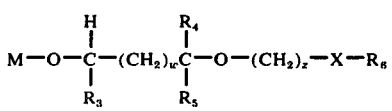   VII wherein $R_3$, $R_4$, $R_5$, $R_6$, X, $w$ and $z$ are as defined above,
with a compound of formula VIII,

LR$_1'$   VIII wherein
L is as defined above, and
$R_1'$ is primary or secondary alkyl of 1 to 9 carbon atoms, primary or secondary alkenyl of 3 to 9 carbon atoms, primary or secondary alkynyl of 3 to 9 carbon atoms, cycloalkyl of 5 to 7 ring carbon atoms, or cycloalkyl of 5 to 7 ring carbon atoms substituted by alkyl of 1 to 4 carbon atoms,
$R_1'$ being bonded to L through a primary or secondary carbon atom,
in the presence of an acid acceptor when M of formula VII is hydrogen, to produce a compound of formula Ic

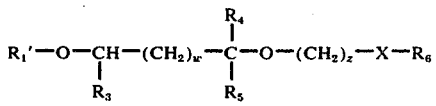   Ic wherein $R_1'$, $R_3$, $R_4$, $R_5$, $R_6$, X, $w$ and $z$ are as defined above, e. condensing a compound of formula IX

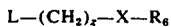   IX wherein L, $z$, X and $R_6$ are as defined above,
with a compound of formula X

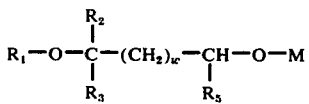   X wherein $R_1$, $R_2$, $R_3$, $R_5$, $w$ and M are as defined above,
in the presence of an acid acceptor when M of formula X is hydrogen, to produce a compound of formula Id

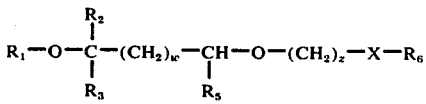   Id wherein $R_1$, $R_2$, $R_3$, $R_5$, $R_6$, X, $w$ and $z$ are as defined above, f. condensing a compound of formula XI

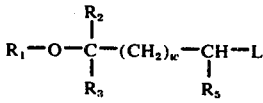   XI wherein $R_1$, $R_2$, $R_3$, $R_5$, $w$ and L are as defined above,
with a compound of formula XII M—O—(CH$_2$)$_z$—X—R$_6$   XII wherein M, $z$, X and $R_6$ are as defined above,
in the presence of an acid acceptor when M of formula XII is hydrogen, to produce a compound of formula Id, or g. condensing a compound of formula IV

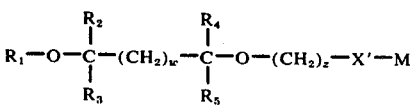   IV wherein
$R_1$, $R_2$, $R_3$, $R_4$, $R_5$, $w$, $z$ and M are as defined above, and
X' is oxygen or sulphur,
with a compound of formula XIII

L'—CH$_2$—R$_6$   XIII wherein
R$_6$ is as defined above, and
L' is chlorine or bromine,
in the presence of an acid acceptor when M of formula IV is hydrogen, to produce a compound of formula Ie,

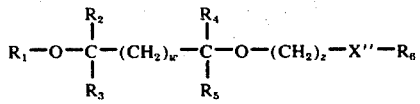

wherein
R$_1$, R$_2$, R$_3$, R$_4$, R$_5$, R$_6$, w and z are as defined above, and
X'' is —OCH$_2$—or —SCH$_2$.

The process of the invention in accordance with variant (a) above may be effected as follows, viz:

The condensation may be effected in a solvent such as a hydrocarbon solvent, e.g. benzene, an ether solvent, e.g. dioxane, 1,2-dimethoxyethane or diethyleneglycoldimethylether, an alcohol solvent e.g. ethanol or tert.butanol, a ketone solvent, e.g. acetone, a nitrile solvent, e.g. acetonitrile, an acid amide solvent e.g. dimethylformamide or hexamethyl phosphoric triamide, or an appropriate mixture of any of the above-mentioned solvents. In the case when M of formula III is hydrogen, an acid binding agent is added, preferably in stoichiometric amount. Examples of suitable acid binding agents are sodium hydroxide, potassium hydroxide, sodium carbonate and potassium tert-.butoxide. The reaction is preferably effected at a temperature between 0° and 100° C. Sodium iodide may advantageously be added to the reaction mixture in catalytic amounts to serve as a catalyst for the reaction.

In a preferred form of the process, the salt form of the compound of formula III (i.e. when M of formula VI is sodium or potassium, especially sodium) is produced in situ e.g. by addition of sodium hydride, preferably under anhydrous conditions and in an inert atmosphere, e.g. in a nitrogen atmosphere. This preferred form of the process is particularly well suited to the compounds of formula II wherein X thereof is —OCH$_2$—.

Working up of the reaction mixture may be effected in conventional manner.

The process of the invention in accordance with variant (b) above may be effected as follows, viz:

The condensation may be effected in a solvent e.g. the solvents exemplified in relation to process variant (a). Preferably, however, the condensation is effected in the absence of a solvent. The reaction is preferably effected at a temperature above room temperature, for example, up to 110° C, preferably between 100° and 110° C. The reaction period is preferably prolonged, for example up to 60 hours, e.g. between 10 and 60 hours, preferably from 18 to 60 hours. The reaction is effected in the presence of dicyclohexylcarbodiimide as condensation agent.

Working up may be effected in conventional manner.

The process of the invention in accordance with variant (c) above, may be effected as follows, viz:

The reaction may be effected in a solvent such as a hydrocarbon solvent e.g. benzene or an ether solvent e.g. dioxane, 1,2-dimethoxyethane or diethyleneglycol dimethylether, or in the absence of a solvent employing an excess of the free alcohol form of the compound of formula VI. The reaction period may vary e.g. from 3 to 15 hours. The reaction temperature is preferably in the range of from room temperature to 100° C.

Working up of the reaction mixture may be effected in manner known per se.

The process in accordance with variant (d) above may be effected as follows, viz:

A compound of formula VII, preferably in sodium or potassium salt form, may be reacted, whilst stirring, with a compound of formula VIII in an anhydrous solvent such as a hydrocarbon solvent, e.g. benzene, an ether solvent, e.g. dioxane, 1,2-dimethoxyethoxy or diethylene glycol dimethylether, a ketone solvent, e.g. acetone, a nitrile solvent, e.g. acetonitrile, or an acid amide solvent, e.g. dimethylformamide or hexamethyl phosphoric triamide, or when M of formula VII is hydrogen, in the absence of a solvent in an excess of the compound of formula VII. When M of formula VII is hydrogen, the reaction is effected in the presence of an acid acceptor, such as sodium hydroxide or potassium tert.butoxide. The reaction temperature will vary, e.g. between 0° and 100° C. preferably from 50° to 100° C. The reaction period varies from between, e.g. 6 and 24 hours.

Preferably, the compound of formula VII in sodium or potassium salt form is produced in situ from the free alcohol form thereof, e.g. by reaction with metallic sodium or sodium hydride, preferably in an inert atmosphere, e.g. a nitrogen atmosphere.

Working up may be effected in conventional manner.

The process in accordance with variant (e) above may be effected as follows, viz:

A compound of formula X, preferably in sodium or potassium salt form, may be reacted whilst stirring with a compound of formula IX, in an anhydrous solvent such as a hydrocarbon solvent, e.g. benzene, an ether solvent, e.g. dioxane, 1,2-dimethoxyethane or diethylene glycol dimethylether, a ketone solvent, e.g. acetone, a nitrile solvent, e.g. acetonitrile or an acid amide solvent, e.g. dimethylformamide or hexamethyl phosphoric triamide, or when M of formula X is hydrogen, in the absence of a solvent in an excess of the compound of formula X. When M of formula X is hydrogen, the reaction is effected in the presence of an acid acceptor, such as sodium hydroxide or potassium tert-.butoxide. The reaction temperature will vary, e.g. between 0° and 100° C preferably from 50° to 100° C. The reaction period varies from between, e.g. 6 and 24 hours.

Preferably, the compound of formula X in sodium or potassium salt form is produced in situ from the free alcohol form thereof, e.g. by reaction with metallic sodium or sodium hydride, preferably in an inert atmosphere, e.g. a nitrogen atmosphere.

Working up may be effected in conventional manner.

The process in accordance with variant (f) above may be effected as follows, viz:

The reaction may be effected in an anhydrous solvent such as a hydrocarbon solvent, e.g. benzene, an ether solvent, e.g. dioxane, 1,2-dimethoxyethane or diethylene glycol dimethylether, a ketone solvent, e.g. acetone, a nitrile solvent, e.g. acetonitrile, or an acid amide, e.g. dimethyl formamide or hexamethyl phosphoric triamide, or when M of formula XII is hydrogen, in the absence of a solvent in an excess of the compound of formula XII. Preferably the compound of formula XII is reacted in sodium or potassium salt form. When the compound of formula XII is reacted in the form of the free alcohol, the reaction is effected in the presence of an acid acceptor, e.g. sodium hydroxide or potassium tert.butoxide. The reaction temperature will vary, e.g. between 0° and 100° C, preferably from 50° to 100° C. The reaction period varies from between, e.g. 6 and 24 hours.

Preferably the compound of formula XII in sodium or potassium salt form is produced in situ from the free alcohol form thereof, e.g. by reaction with metallic sodium or sodium hydride, preferably in an inert atmosphere, e.g. a nitrogen atmosphere.

Working up may be effected in conventional manner.

The process in accordance with process variant (g) above may be effected as follows, viz:

The reaction may be effected in a solvent such as a hydrocarbon solvent, e.g. benzene, an ether, e.g. 1,2-dimethoxyethane, an alcohol, e.g. ethanol or tert-.butanol, a ketone, e.g. acetone, a nitrile, e.g.acetonitrile, or an acid amide, e.g. dimethylformamide, or in the absence of a solvent. When M of formula IV is hydrogen, the reaction is effected in the presence of an acid binding agent such as sodium bicarbonate, sodium carbonate, sodium hydroxide or potassium hydroxide. The reaction temperature varies from about 20° to 120° C.

The compound of formula IV in sodium or potassium salt form may be produced in situ from the free alcohol form thereof, e.g. by reaction with sodium hydride, preferably in an inert atmosphere, e.g. in a nitrogen atmosphere.

Working up of the reaction mixture may be effected in conventional manner.

The compounds of formula II, employed as starting materials in process variant (a) above, are either known, or may be produced in accordance with processes known per se, e.g.

a'. by condensing a compound of formula XIV with

 L(CH$_2$)$_z$L      XIV wherein L and z are as defined above,
with a compound of formula X, under analogous reaction conditions to those described above in relation to process variants (d), (e) or (f), to produce a compound of formula IIa

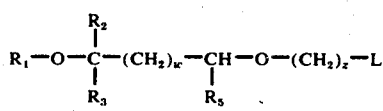

wherein R$_1$, R$_2$, R$_3$, R$_5$, w, z and L are as defined above, b'. by halogenating a compound of formula IVa with an halogenating agent under conditions which avoid ether cleavage, [Houben-Weyl,Methoden der Organischen Chemie, Vol V/4, pages 361–411 (1960), and Vol V/3 pages 862, 899, 905 and 932 (1962), Georg Thieme], e.g. with thionyl chloride or bromide or with phosphoric chloride or bromide, to produce a compound of formula IIb

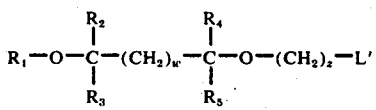

wherein R$_1$, R$_2$, R$_3$, R$_4$, R$_5$, w, z and L' are as defined above,
or c'. reacting a compound of formula IVa with tosylchloride in the presence of an acid acceptor, e.g. anhydrous sodium carbonate, sodium hydroxide, zinc oxide or pyridine [Houben-Weyl, Methoden der Organischen Chemie, Vol IX, pages 643–668, (1955) Georg Thieme], to produce a compound of formula IIc,

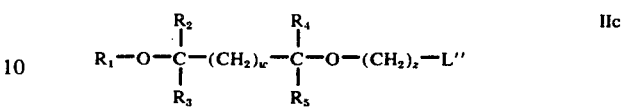

wherein
R$_1$, R$_2$, R$_3$, R$_4$, R$_5$, w and z are as defined above, and
L'' is tosyl.

The compounds of formula IV are known or may be produced in manner known per se. For example, the compounds of formula IVa',

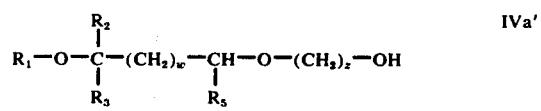

wherein R$_1$, R$_2$, R$_3$, R$_5$, w and z are as defined above, may be produced in manner known per se by reacting a compound of formula XI with a compound of formula XV,

 M'O(CH$_2$)$_z$OH      XV wherein
z is as defined above, and
M' is sodium or potassium,
under the reaction conditions described above in relation to process variants (d), (e) and (f).

The compounds of formula IVb

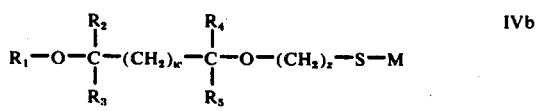

wherein R$_1$, R$_2$, R$_3$, R$_4$, R$_5$, w, z and M are as defined above
may, for example, be produced in manner known per se by reacting a compound of formula II with thiourea in alcohol at reflux or alternatively, with ammonium dithiocarbamate with hydrolysis of the resulting product.

The compounds of formula IX are either known or may be produced in manner known per se. For example the compounds of formula IXa,

 L(CH$_2$)$_z$—X'''—R$_6$      IXa wherein
L, z and R$_6$ are as defined above, and
X''' is oxygen or —O—CH$_2$—,
may be produced by reacting a compound of formula XIV with the appropriate compound of formula III under the reaction conditions described above in relation to process variant (a). In addition, the compounds of formula IXb

 L'(CH$_2$)$_z$—X—R$_6$      IXb wherein L', z, X and R$_6$ are as defined above,
may, for example, be produced by reacting a compound of formula XIIa $$HO-(CH_2)_z-X-R_6 \qquad \text{XIIa}$$

wherein z, X and $R_6$ are as defined above,
with an appropriate halogenating agent in analogous manner to that described above in relation to process (b') above.

The compounds of formula X are either known or may be produced in manner known per se. For example, the compounds of formula X may be produced by reducing a compound of formula XVI.

$$R_1-O-\underset{\underset{R_3}{|}}{\overset{\overset{R_2}{|}}{C}}-(CH_2)_w-\overset{\overset{O}{\|}}{C}-R_5 \qquad \text{XVI}$$

wherein $R_1$, $R_2$, $R_3$, $R_5$ and w are as defined above,
with sodium borohydride in conventional manner.

The compounds of formula Xa $$R_1'-O-\underset{\underset{R_3}{|}}{CH}-(CH_2)_w-\underset{\underset{R_3}{|}}{CH}-O-M \qquad \text{Xa}$$

wherein $R_1'$, $R_3$, w and M are as defined above,
the two $R_3$ substituents being the same, may, for example, be produced by reacting a compound of formula XVII, $$M'O-\underset{\underset{R_3}{|}}{CH}-(CH_2)_w-\underset{\underset{R_3}{|}}{CH}-OH \qquad \text{XVII}$$

wherein $R_3$, w and M' are as defined above,
with a compound of formula VIII under reaction conditions analogous to those described in relation to process variant (d) above. The compounds of formula XI are either known or may be produced in manner known per se.

For example, the compounds of formula XIa $$R_1-O-\underset{\underset{R_3}{|}}{CH}-(CH_2)_w-\underset{\underset{R_3}{|}}{CH}-L \qquad \text{XIa}$$

wherein $R_1$, $R_3$, w and L are as defined above,
the two $R_3$ substituents being the same, may be produced by reacting a compound of formula XVIII $$L-\underset{\underset{R_3}{|}}{CH}-(CH_2)_w-\underset{\underset{R_3}{|}}{CH}-L \qquad \text{XVIII}$$

wherein L, $R_3$ and w are as defined above,
with a compound of formula VI under reaction conditions analogous to those described in relation to process variant (c) above.

The compounds of formula XII are either known or may be produced in manner known per se.

For example, the compounds of formula XIIa may be produced by reacting a compound of formula XIX $$HO-(CH_2)_z-L \qquad \text{XIX}$$

wherein z and L are as defined above,
with a compound of formula III.

Insofar as the production of starting materials has not been described, these are known or may be produced in accordance with processes known per se or in analogous manner to the processes described herein or to the processes known per se.

The compounds of formula I are generally colourless oils or occasionally low melting point crystalline solids.

The compounds of formula I possess insecticidal and acaricidal properties in the sense that they exhibit an inhibiting effect on the development of insects and acarids from one development stage thereof to the next, to result either in death, reduced oviposition or inhibition of copulation and thereby to a reduced insect or acarid population. The above-mentioned effect of the compounds of formula I is indicated by the following tests, viz:

TEST 1

Insecticidal Effect on *Dysdercus fasciatus* Larvae
(Egyptian cotton worm)

Filter paper is impregnated with a solution of the active agent of formula I (0.1 mg/cm$^2$). A box made from polystyrene (200 × 100 × 85 mm) is coated with the filter paper treated in this way. A folded filter paper, which is also impregnated, is covered with about 30 Dysdercus larvae of the 4th larval stage and placed into the box. Pounded cotton seeds, as food, and a drinking vessel are placed into the box. The rate of development is determined about 10 days. The rate of development of the Dysdercus larvae into adults was found to be substantially reduced or inhibited

TEST 2

Insecticidal Effect on the Development of *Prodenia littura* Larvae (cotton stainer) into Adults Filter paper is impregnated with a solution of the active agent of formula I (0.1 mg/cm$^2$). Compartments of a plastic box are coated with the filter paper treated in this way. One Prodenia caterpillar is placed into each compartment and a piece of artificial medium is given as food. The number of the normally developed adults is determined after 21 days. The rate of development of the larvae into adults is found to be substantially reduced or inhibited.

TEST 3

Acaricidal Contact Effect in *Tetranychus urticae* (red spider mite)

One day before treatment, 10 adult females of *Tetranychus urticae* are placed by means of a fine brush between two rings (diameter: 3 cm) of caterpillar glue which are applied to a leaf of a cotton plant. The cotton leaves are sprayed to run off by means of a sprayer with a liquor containing 0.1 % of active agent. The liquor is allowed to dry and then the plants are kept at room temperature and in light. The dead and live insects are counted 6 days after the treatment. The ratio between the treated and an untreated population indicates the effect. The results indicate a substantial reduction or inhibition of oviposition.

Aside from their insecticidal and acaricidal effects, the compounds of formula I exhibit only low mammalian toxicity.

The compounds of formula I are therefore useful as insecticides and acaricides, particularly in applications where low mammalian toxicity is desirable, e.g. in plant protection.

For the abovementioned use, the amount applied to a locus to be treated will of course vary depending on the compound employed, the mode of application, ambient conditions, and the insects or acarids to be combated. However, with regard to plant protection, satisfactory results are obtained when applied to a plant locus in an amount of between 1 and 4 kg hectare, the application being repeated as required.

The compounds may be applied to the locus with conventional applicator equipment and by conventional methods e.g. strewing, spraying and dusting.

Compositions may comprise a compound of formula I in admixture with insecticidal or acaricidal carriers, diluents and/or adjuvants in solid or liquid form e.g. spraying and dusting powders, granulates, liquid sprays and aerosols.

Solid forms may include diluents and carriers such as diatomaceous earth, bentonite and pumice. Adjuvants e.g. surfactants such as wetting and dispersing agents and adhesive agents, e.g. cellulose derivatives, may also be included in the case of wettable powders to be applied as a water suspension. Granulates are produced by coating or impregnating granular carrier materials such as pumice, limestone, attapulgite and koalinite with the compounds.

Liquid forms may include non-phyotoxic diluents and carriers such as alcohols, glycolic ethers, e.g. isooctyphenyloctaglycolether aliphatic and aromatic hydrocarbons e.g. xylene, alkyl napthalenes and other petroleum distillates. Adjuvants such as surface active agents, e.g. wetting and emulsifying agents such as polyglycol ethers formed by the reaction of an alkylene oxide with high molecular weight alcohols, mercaptans or alkyl phenols, may be included in emulsion concentrate forms. Appropriate organic solvents e.g. ketones, aromatic optionally halogenated hydrocarbons and mineral oils may also be included as solvent aids.

Aside from the abovementioned carriers, diluents and adjuvants, adjuvants such as U.V. stabilizing agents, antioxidants, desactivators (for solid forms with carriers having an active surface), agents for improving adhesiveness to surfaces treated, anticorrosives, defoaming agent, evaporation reducing agents, and pigments may also be included.

Concentrate forms of composition generally contain between 2 and 90 %, preferably between 5 and 50 %, by weight of active compound.

Application forms of composition generally contain between 0.01 and 10%, and preferably between 0.01 and 0.4%, e.g. between 0.01 and 0.1%, by weight of active compound.

Examples of concentrate forms of composition will now be described, viz:

a. Emulsifiable Concentrate

25 Parts by weight of a compound of formula I are mixed with 25 parts by weight of isooctylphenyldecaglycol ether and 50 parts by weight of xylene, whereby a clear solution is obtained which may be readily emulsified in water. The concentrate may be diluted with water to the desired concentration.

b. Emulsifiable Concentrate

25 Parts by weight of a compound of formula I are mixed with 30 parts by weight of isooctylphenyloctaglycol ether and 45 parts by weight of a petroleum fraction having a B.P. of 210–280° ($D_{20}$ : 0.92). The concentrate may be diluted with water to the desired concentration.

c. Emulsifiable Concentrate

50 Parts by weight of a compound of formula I are mixed with 50 parts by weight of isooctylphenyloctaglycol ether. A clear concentrate is obtained which may be readily emulsified in water and which may be diluted with water to the desired concentration.

A preferred group of compounds of formula I are generally those compounds of formula I wherein, $R_1$ is alkyl of 1 to 9 carbon atoms, particularly branched or secondary alkyl of 3 to 9 carbon atoms, $R_2$, $R_3$, $R_4$ and $R_5$ are each, independently, hydrogen or alkyl of 1 to 4 carbon atoms, particularly when one of $R_2$ and $R_3$ and/or $R_4$ and $R_5$ is hydrogen, $w$ is an integer 2 to 4, $z$ is an integer 2 to 6, $X$ is oxygen, sulphur, a group —OCH$_2$— or —SCH$_2$—, particularly oxygen or a group —OCH$_2$—, and $R_6$ is an aromatic radical $Ar_1'$

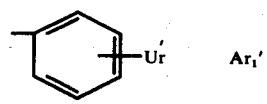

wherein $U'$ is alkyl of 1 to 6 carbon atoms, particularly of 1 to 4 carbon atoms, or alkylthio of 1 to 6 carbon atoms, particularly of 1 to 4 carbon atoms, and $r$ is an integer 1 or 2, preferably 1.

Another preferred group of compounds of formula I are generally those compounds of formula I wherein, $R_1$ is alkyl of 1 to 9 carbon atoms, particularly branched or secondary alkyl of 3 to 9 carbon atoms, $R_2$, $R_3$, $R_4$ and $R_5$ are each independently hydrogen or alkyl of 1 to 4 carbon atoms, particularly when one of $R_2$ and $R_3$ and/or $R_4$ and $R_5$ is hydrogen, $w$ is an integer 2 to 4, $z$ is an integer 2 to 6, $X$ is oxygen, sulphur, a group —OCH$_2$—or —SCH$_2$ particularly oxygen or a group —OCH$_2$—, and $R_6$ is an aromatic radical $Ar_2'$,

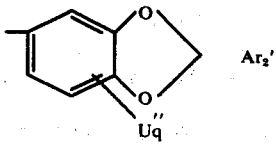

wherein $U''$ is alkyl of 1 to 6 carbon atoms, particularly of 1 to 4 carbon atoms, or alkylthio of 1 to 6 carbon atoms, particularly 1 to 4 carbon atoms, and $q$ is zero or an integer 1 or 2, preferably zero.

Examples of the process for producing the novel compounds of the invention are as follows. Where temperature is referred to, this is in degrees Centigrade.

EXAMPLE 1

1-Ethyl-4-[4-(4-isopentyloxy-butyloxy)-butyloxy]-benzene (process a)) 0.43 g (0.0078 mol) of solid potassium hydroxide are added while stirring to 0.65 g (0.0053 mol) of 4-ethylphenol in 20 cc of absolute dimethylformamide. The solution is stirred for 30 minutes at 20° and then 1.50 g (0.0051 mol) of 1-bromo-4-(4-isopentyloxy-butyloxy)-butane are added dropwise. The mixture is subsequently stirred at 20° for 20 hours. The reaction product is taken up in ether, washed with ice-cold 1N sodium hydroxide solution, water and saturated sodium chloride solution, dried over sodium sulphate and evaporated. After chromatography of the residue on silica gel with hexane/ethyl acetate (97:3), 1-ethyl-4-[4-(4-isopentyloxy-butyloxy)-butyloxy]-benzene is obtained as a colourless oil.

$n_D^{20} = 1.4802$
Analysis: $C_{21}H_{36}O_3$    Molecular weight: 336.5
Calc.    C 75.0 %    H 10.8 %    O 14.3 %
Found    74.5 %    10.9 %    14.7 %

In analogous manner to that described in Example 1 using the appropriate starting materials, the following compounds are produced, viz
a. 1-methyl-4-[4-(4-propargyloxy-butyloxy)-butyloxy]-benzene,
b. 1-ethyl-4-[4-(4-cyclohexyloxy-butyloxy)-butyloxy]benzene,
c. 1-ethyl-4-{4-[4-(3-methyl-cyclohexyloxy)-butyloxy]-butyloxy}-benzene,
d. 1-ethyl-4-[4-(4-isopentyloxy-butyloxy)-butylthio]-benzene,
e. 1-allyl-4-[6-(4-isopentyloxy-butyloxy)-hexyloxy]-benzene,
f. 1-[6-(4-isopentyloxy-butyloxy)-hexyloxy]-4-methoxybenzene,
g. 1-allyloxy-4-[6-(4-isopentyloxy-butyloxy)-hexyloxy]-benzene,
h. 4-[6-(4-isopentyloxy-butyloxy)-hexyloxy]-benzoic acid-N,N-dimethylamide,
i. 1-[6-(4-isopentyloxy-butyloxy)-hexyloxy-methyl]-4-methoxymethyl)-benzene,
j. 1-chloro-4-[6-(4-isopentyloxy-butyloxy)-hexyloxymethyl]-benzene, and
k. 1-bromo-4-[6-(4-isopentyloxy-butyloxy)-hexyloxymethyl]-benzene.

EXAMPLE 2

[4-(4-Isopentyloxy-butyloxy)-butyl]-piperonyl ether (process a)

To a solution of 1.23 g (0.0081 mol) of piperonyl alcohol and 2.50 g (0.0085 mol) of 1-bromo-4-(4-isopentyloxy-butyloxy)-butane in 30 cc of absolute 1,2-dimethoxy-ethane, there is carefully added under nitrogen and while stirring, over the course of 20 minutes, 0.34 g (0.0077 mol) of 55% sodium hydride dispersion in oil. The mixture is stirred at 60° for 20 hours and the resulting sodium bromide is subsequently suction filtered, washed with ether and the filtrate is evaporated. After chromatography of the residue on silica gel with hexane/ethyl acetate (97:3) to (9:1), the [4-(4-Isopentyloxy-butyloxy)-butyl]-piperonyl ether is obtained as a colourless oil.

$n_D^{20} = 1.4852$
Analysis: $C_{21}H_{34}O_5$    Molecular weight: 366.5
Calc.    C 68.8 %    H 9.4 %    O 21.8 %
Found    68.1 %    9.3 %    22.5 %

EXAMPLE 3

6-[4-(5-Allyloxy-2-hexyloxy)-butyloxy]-1,3-benzodioxol (process a)

The compound may be produced in analogy to Example 1 but using 1-bromo-4-(5-allyloxy-2-hexyloxy)-butane $n_D^{20} = 1.5020$
Analysis: $C_{20}H_{30}O_5$    Molecular weight: 350.5
Calc.    C 68.5 %    H 8.6 %    O 22.8 %
Found    68.2 %    8.7 %    22.5 %

In analogous manner to that desired described in Example 3, using the appropriate starting materials, the following compounds are produced, viz:
a. 5-allyl-6-[6-(4-isopentyloxy-butyloxy)-hexyloxy]-2,2-dimethyl-1,3-benzodioxol,
b. 5'[6-(4-isopentyloxy-butyloxy)-hexyloxy]-2,3-methylenedioxy-benzoic acid-M,N-dimethylamide, and
d. 5-[6-(4-isopentyloxy-butyloxy)-hexyloxy]-6-chloro-1,3-benzodioxol,

EXAMPLE 4

1-Ethyl-4-[6-(4-isopentyloxy-butyloxy)-hexyloxy]-benzene (process b)

2.60 g (0.010 mol) of 6-(4-Isopentyloxybutyloxy)-hexanol are mixed with 1.22 g (0.010 mol) of 4-ethylphenol and 2.06 g (0.010 mol) of dicyclohexyl carbodiimide and the mixture is stirred at 100° C over the course of 3 days. After cooling the residue is chromatographed with hexane/ethyl acetate (97:3) on silica gel, whereupon 1-ethyl-4-[6-(4-isopentyloxybutyloxy)-hexyloxy]-benzene is obtained, which according to thin layer chromatography and gas-chromatography is a pure oil.

$n_D^{20} = 1.4762$
Analysis: $C_{23}H_{40}O_3$    Molecular weight: 364.6
Calc.    C 75.8 %    H 11.1 %    O 13.2 %
Found    75.4 %    10.7 %    13.5 %

EXAMPLE 5

[6-(4-Isopentyloxy-butyloxy)-hexyl]-piperonyl ether (process g)

0.60 g (0.020 mol) of 80% sodium hydride dispersion are added by portions, at 20°, under nitrogen and while stirring, to 4.02 g (0.0155 mol) of 6-(4-Isopentyloxybutyloxy)-hexanol in 60 cc of absolute 1,2-dimethoxyethane. The mixture is stirred at 60° over the course of 2 hours, cooled to 0° and a solution of 3.65 g (0.017 mol) of piperonyl bromide in 40 cc of absolute 1,2-dimethoxy ethane is added dropwise over the course of 10 minutes. The mixture is stirred at 20° for 3 hours and then at 40° for 20 hours, neutralized with 6N sulphuric acid and together with 1.35 g (0.017 mol) of pyridine heated to 60° over the course of 2 further hours. The reaction product is taken up in ether, washed with water, 6N sulphuric acid, water and saturated sodium chloride solution, dried over magnesium sulphate and evaporated. After chromatography of the residue on silica gel with hexane/acetone (98:2) and (96:4), [6-(4-Isopentyloxybutyloxy)-hexyl]-piperonyl ether is obtained as a colourless oil.

| $n_D^{20} = 1.4867$ | | | |
|---|---|---|---|
| Analysis: | $C_{23}H_{38}O_5$ | | Molecular weight: 394.6 |
| Calc. | C 70.0 % | H 9.7 % | O 20.3 % |
| Found | 69.5 % | 9.7 % | 20.6 % |

The compound may also be produced in analogy to Example 2.

EXAMPLE 6

[6-(6-Isopentyloxy-hexyloxy)-hexyl]-piperonyl ether (process g)

2.88 g (0.010 mol) of 6-(6-Isopentyloxyhexyloxy)-hexanol are mixed with 2.15 g (0.010 mol) of piperonyl bromide and 1.26 g (0.015 mol) of sodium bicarbonate and the mixture is stirred at 80° for 18 hours and then at 120° C for 6 hours. 1.0 cc of pyridine is added to the reaction mixture which is heated to 80° over the course of 2 hours. The reaction mixture is cooled, taken up in ether, washed with 2N sulphuric acid, water and saturated sodium chloride solution, dried over magnesium sulphate and evaporated. After chromatography of the residue on silica gel with hexane/acetone (98:2) and (96:4), [6-(6-Isopentyloxyhexyloxy)-hexyl]-piperonyl ether is obtained as a colourless oil.

| $n_D^{20} = 1.4902$ | | |
|---|---|---|
| Analysis: | $C_{27}H_{42}O_5$ | Molecular weight: 442.6 |
| Calc. | C 71.1 % | H 10.0 % |
| Found | 70.5 % | 9.9 % |

The compound may also be produced in analogous manner to that described in Example 2.

EXAMPLE 7

1-[4-(4-Isopropoxy-butyloxy)-butyloxy]-4-(methylthio)-benzene (process e)

0.320 g (7.35 millimols) of 55% sodium hydride dispersion in oil are added by portions, over the course of 15 minutes and while stirring, to 1.02 g (7.7 millimols) of 4-isopropoxybutanol and 1.82 g (7.0 millimols) of 1-(4-bromo-butyloxy)-4-(methylthio)-benzene in 20 cc of absolute 1,2-dimethoxy ethane. The mixture is stirred at 20° for 18 hours and subsequently at 60° for 6 hours. The resulting sodium bromide is suction filtered, washed with ether and the filtrate is evaporated. After chromatography of the residue on silica gel with hexane/ethyl acetate (97:3) and (95:5), 1-[4-(4-isopropoxy-butyloxy)-butyloxy]-4-(methylthio)-benzene is obtained as a colourless oil.

| $n_D^{20} = 1.5040$ | | | |
|---|---|---|---|
| Analysis: | $C_{18}H_{30}O_3S$ | | Molecular weight: 326.5 |
| Calc. | C 66.2 % | H 9.3 % | S 9.8 % |
| Found | 66.6 % | 9.4 % | 9.5 % |

The following compound of general formula I may be produced in analogous manner to that described in Example 7:

EXAMPLE 8

1-[4-Isopentyloxy-butyloxy)butyloxy]-4-(methylthiobenzene (process e)

Using 4-isopentyloxy-butanol and 1-(4-bromobutyloxy)-4-(methylthio)-benzene, the above compound may be produced.

| $n_D^{20} = 1.5083$ | | | |
|---|---|---|---|
| Analysis: | $C_{20}H_{34}O_3S$ | | Molecular weight: 354.6 |
| Calc. | C 67.8 % | H 9.7 % | S 9.0 % |
| Found | 67.8 % | 9.8 % | 9.2 % |

EXAMPLE 9:

[2-(4-Isopropoxy-butyloxy)-ethyl]-piperonyl-thioether (process f)

2.12 g (0.01 mol) of 2-piperonylthioethanol are added at room temperature over the course of 10 minutes, to a suspension of 0.48 g (0.01 mol) of 50% sodium hydride dispersion, which had been freed from the mineral oil with hexane, in 40 cc of 1,2-dimethoxy ethane. The mixture is stirred at 50° l for 3 hours and a solution of 1.95 g (0.01 mol) of 1-bromo-4-isopropoxybutane in 30 cc of 1,2-dimethoxy ethane is subsequently added. The mixture is stirred at 60° over the course of 48 hours. After cooling to 20°, 100 cc of ether are added to the reaction mixture. The ether solution is extracted with saturated sodium chloride solution, dried over sodium sulphate and evaporated. The residue is purified by chromatography on silica gel with hexane/ethyl acetate (5:1), whereupon [2-(4-isopropoxy-butyloxy)-ethyl]-piperonylthioether is obtained as a slightly yellow, clear oil.

| $n_D^{20} = 1.5215$ | | | |
|---|---|---|---|
| Analysis: | $C_{17}H_{26}O_4S$ | | Molecular weight: 326.5 |
| Calc. | C 62.5 % | H 8.0 % | O 19.6 % S 9.8 % |
| Found | 62.3 % | 8.0 % | 19.6 % 10.2 % |

The starting materials of general formula II may, for example, be produced in accordance with the following process:

EXAMPLE 10

1-Bromo-4-(4-isopentyloxy-butyloxy)-butane 1.77 g (0.041 mol) of 55% sodium hydride dispersion in oil are carefully added over the course of 40 minutes, under nitrogen and while stirring, to 26.0 g (0.163 mol) of 4-isopentyloxy-butanol. The mixture is stirred at 60° for 30 minutes and 11.4 g (0.053 mol) of 1,4-dibromobutane are subsequently added dropwise and it is stirred at 60° for 20 hours. The resulting sodium bromide is suction filtered, washed with ether and the filtrate is evaporated. The residue is fractionally distilled in a high vacuum and apart from the excess 4-isopentyloxy butanol, 1-bromo-4-(4-isopentyloxy-butyloxy)-butane, having a B.P. of 121–123°/0.7 mm Hg, is obtained as a colourless liquid.

| Analysis: | $C_{13}H_{27}BrO_2$ | Molecular weight: 295.3 |
|---|---|---|

-continued

| | | | |
|---|---|---|---|
| Calc. | C 52.9 % | H 9.2 % | Br 27.1 % |
| Found | 53.7 % | 9.0 % | 26.4 % |

The following compounds of general formula II may be produced in analogous manner to that described in Example 10:

EXAMPLE 11

1-Bromo-6-(4-isopentyloxy-butyloxy)-hexane

Using 4-isopentyloxy butanol and 1,6-dibromo-hexane, the above compound is produced. B.P.: 142°–145°/0.7 mm.

| Analysis: | $C_{15}H_{31}BrO_2$ | | Molecular weight: 323.2 |
|---|---|---|---|
| Calc. | C 55.7 % | H 9.7 % | Br 24.7 % |
| Found | 56.0 % | 9.6 % | 24.9 % |

EXAMPLE 12

1-Bromo-4-(5-allyloxy-2-hexyloxy)-butane

Using 5-allyloxy-2-hexanol and 1,4-dibromo-butane, the above compound is produced.

| $n_D^{20} = 1.4656$ | | | |
|---|---|---|---|
| Analysis: | $C_{13}H_{25}BrO_2$ | | Molecular weight: 293.3 |
| Calc. | C 53.2 % | H 8.6 % | Br 27.3 % |
| Found | 53.0 % | 8.6 % | 27.6 % |

The starting materials of general formula IV may, for example, be produced in accordance with the following process:

EXAMPLE 13

6-(4-Isopentyloxy-butyloxy)-hexanol 17.8 g (0.163 mol) of 1,6-hexandiol in 30 cc of absolute 1,2-dimethoxy ethane are added dropwise over the course of 15 minutes, under nitrogen and while stirring, to 4.85 g (0.117 mol) of 55% sodium hydride dispersion in oil, suspended in 140 cc of absolute 1,2-dimethoxy ethane. The mixture is stirred at 60° for 3 hours, 22.5 g (0.101 mol) of 1-bromo-4-isopentyloxy-butane are then added and then it is stirred at 60° for 40 hours. After cooling to 20°, 400 cc of ether are added to the reaction mixture. The ether solution is washed three times with water, subsequently with saturated sodium chloride solution, dried over sodium sulphate and evaporated. The residue is chromatographed with hexane/ethyl acetate (95:5) to (75:25) on silica gel. The almost pure fractions are fractionally distilled and 6-(4-isopentyloxy-butyloxy)-hexanol, having a B.P. of 134°–142°/0.5 mm Hg, is obtained as a colourless liquid.

| Analysis: | $C_{15}H_{32}O_3$ | | Molecular weight: 260.4 |
|---|---|---|---|
| Calc. | C 69.2 % | H 12.4 % | O 18.4 % |
| Found | 68.8 % | 12.4 % | 18.7 % |

EXAMPLE 14

6-(6-Isopentyloxy-hexyloxy)-hexanol

The above compound may be produced in analogous manner to that described in Example 13, but using 1-bromo-6-isopentyloxy hexane and 1,6-hexandiol.

| $n_D^{20} = 1.4498$ | | | |
|---|---|---|---|
| Analysis: | $C_{17}H_{36}O_3$ | | Molecular weight: 288.5 |
| Calc. | C 70.8 % | H 12.6 % | O 16.6 % |
| Found | 70.5 % | 12.3 % | 16.9 % |

The starting materials of general formula X, required for the production of the compounds of general formulae II and IV, may, for example, be produced in accordance with the following process:

EXAMPLE 15

4-Isopentyloxy butanol

To 12.2 g (0.279 mol) of 55% sodium hydride dispersion in oil, suspended in 400 cc of absolute 1,2-dimethoxy ethane, there is added dropwise, under nitrogen, over the course of 20 minutes and while stirring, 360 g (0.40 mol) of 1,4-butandiol in 50 cc of absolute 1,2-dimethoxy ethane. The mixture is stirred at 60° C for 3 hours, 40.2 g (0.266 mol) of isopentyl bromide are then added and the mixture is stirred at 60° for 22 hours. The resulting sodium bromide is suction filtered, washed with ether and the filtrate is evaporated. For the removal of the excess 1,4-butandiol the residue is taken up in ether, washed three times with water, dried over sodium sulphate and evaporated. After the fractional distillation of the product, pure 4-isopentyloxy butanol, having a B.P. of 80°–81°/0.6 mm Hg, is obtained.

| Analysis: | $C_9H_{20}O_2$ | | Molecular weight: 160.3 |
|---|---|---|---|
| Calc. | C 67.5 % | H 12.6 % | O 20.0 % |
| Found | 67.3 % | 12.5 % | 19.8 % |

The following compounds of general formula X may be produced in analogous manner to that described in Example 15:

EXAMPLE 16

6-Isopentyloxy hexanol

Using 1,6-hexandiol and isopentylbromide, the above compound is produced. B.P.: 164°–170°/12 mm Hg.

EXAMPLE 17 4-Isopropoxy-butanol

Using 1,4- butandiol and isopropylbromide, the above compound is produced.

| Analysis: | $C_7H_{16}O_2$ | Molecular weight: 132.2 |
|---|---|---|
| Calc. | C 63.6 % | H 12.2 % |
| Found | 63.7 % | 12.2 % |

EXAMPLE 18

5-Allyloxy-2-hexanol 12.0 g (0.25 mol) of 50% sodium hydride dispersion in mineral oil are freed from the mineral oil with hexane and covered with a layer of 150 cc of absolute 1,2-dimethoxy ethane. A solution of 35.4 g (0.3 mol) of 2,5-hexandiol in 60 cc of absolute 1,2-dimethoxy ethane is added at 5°–10° over a period of 90 minutes and while stirring to the resulting suspension. After stirring for 2 hours at 50°, the mixture is cooled to 10° and 24.2 g (0.2 mol) of allyl-bromide in 40 cc of dry 1,2-dimethoxy ethane are added dropwise. The mixture is slowly heated to 60° and stirred at this temperature for 16 hours. After this period the reaction mixture is cooled to room temperature. After adding 200 cc amounts of ether and water the mixture is vigorously stirred for 15 minutes and the organic phase is separated off in a separating funnel. The ether extract is washed with saturated salt solution, dried over sodium sulphate and evaporated. The residue is purified by chromatography on silica gel with hexane/ethyl acetate (2:1), whereby, according to gas-chromatography, pure 5-allyloxy-2-hexanol is obtained as a colourless oil.

| | | |
|---|---|---|
| $n_D^{20} = 1.4423$ | B.P.: 62–63°/0.75 mm | |
| Analysis: $C_9H_{18}O_2$ | Molecular weight: 158.2 | |
| Calc. C 68.3 % | H 11.5 % | O 20.2 % |
| Found 68.4 % | 11.1 % | 20.3 % |

The starting materials of general formula IX may, for example, be produced in accordance with the following processes known per se:

EXAMPLE 19

1-(4-Bromo-butyloxy)-4-(methylthio)-benzene 7.0 g (0.05 mol) of 4-(methylthio)-phenol are stirred in 80 cc of absolute dimethylformamide for 30 minutes with 2.8 g (0.05 mol) of pulverized potassium hydroxide. 16.2 g (0.075 mol) of 1,4-dibromo butane are added dropwise over the course of 15 minutes and the mixture is stirred at 20° for 16 hours. After the addition of approximately 150 cc of water, the reaction mixture is extracted with ether, the extract is washed with ice-cold 1N sodium hydroxide solution and saturated sodium chloride solution, dried over sodium sulphate and evaporated. After chromatography of the residue on silica gel with hexene/ethylacetate (99:1) and (98:2) and subsequent crystallization from petroleum ether, pure 1-(4-bromo-butyloxy)-4-(methylthio)-benzene is obtained. M.P.: 33°–34° C.

| | | |
|---|---|---|
| Analysis: $C_{11}H_{15}BrOS$ | Molecular weight: 275.2 | |
| Calc. C 48.0 % | H 5.6 % | Br 29.1 % S 11.6 % |
| Found 48.2 % | 5.6 % | 29.1 % 11.8 % |

The starting materials of general formula XI, required for the production of the compounds of general formulae I and IV, may be produced in similar way as the compounds of general formula II:

EXAMPLE 20

1-Bromo-4-isopropoxy-butane

The above compound is produced in analogous manner to that described in Example 10, but using isopropanol and 1,4-dibromo butane and sodium instead of sodium hydride. B.P.: 90°–91°/34 mm Hg.

| | | |
|---|---|---|
| Analysis: $C_7H_{15}BrO$ | Molecular weight: 195.1 | |
| Calc. C 43.1 % | H 7.7 % | Br 41.0 % |
| Found 43.2 % | 7.6 % | 41.3 % |

EXAMPLE 21

6-Bromo-6-isopropoxy-hexane

The above compound is produced in analogy to Example 10, using isopropanol and 1,6-dibromohexane and sodium instead of sodium hydride. B.P.: 96°–98°/15 mm Hg.

| | | |
|---|---|---|
| Analysis: $C_9H_{19}BrO$ | Molecular weight: 223.2 | |
| Calc. C 48.4 % | H 8.6 % | Br 35.8 % |
| Found 48.7 % | 8.4 % | 35.9 % |

The starting materials of general formula XI may, for example, be produced in accordance with the following process:

EXAMPLE 22

1-Bromo-4-isopentyloxy-butane 6.1 cc (0.0636 mol) of phosphoric tribromide are added dropwise at 0° over the course of 20 minutes and while stirring, to a solution of 27.5 g (0.172 mol) of 4-isopentyloxy-butanol (production: see Example 15) and 1.36 g (0.0172 mol) of pyridine in 150 cc of absolute chloroform. The cooling bath is removed, the mixture is then heated to 60° for 1 hour and stirred at this temperature for 18 hours. The reaction mixture is poured into ice-cold sodium bicarbonate solution, the chloroform phase is removed in a separating funnel, washed with water and saturated sodium chloride solution, dried over magnesium sulphate and evaporated. The residue is filtered with hexane/ethyl acetate (98:2) on silica gel. The evaporated filtrate is fractionally distilled and pure 1-bromo-4-isopentyloxy-butane is obtained. B.P.: 96°–97°/12 mm Hg.

| | | |
|---|---|---|
| Analysis: $C_9H_{19}BrO$ | Molecular weight: 223.2 | |
| Calc. C 48.4 % | H 8.6 % | Br 35.8 % O 7.2 % |
| Found 48.9 % | 8.6 % | 35.4 % 7.4 % |

EXAMPLE 23

1-Bromo-6-isopentyloxy-hexane

The above compound is synthesized in analogous manner to that described in Examle 22, but using 6-isopentyloxy hexanol (production see Example 16). B.P.: 123°–129°/11 mm Hg.

| | | |
|---|---|---|
| Analysis: $C_{11}H_{23}BrO$ | Molecular weight: 251.2 | |
| Calc. C 52.6 % | H 9.2 % | Br 31.8 % |
| Found 52.2 % | 8.7 % | 31.1 % |

The starting materials of general formula XII may, for example, be produced according to the following process:

EXAMPLE 24

2-Piperonylthio-ethanol 0.96 g (0.02 mol) of 50% sodium hydride dispersion are freed from the mineral oil with absolute tetrahydrofuran and suspended in 30 cc of tetrahydrofuran. A solution of 1.56 g (0.02 mol) of 2-mercaptoethanol in 10 cc of tetrahydrofuran is added at 20°–25°while stirring, to this suspension. The mixture is stirred at 60° over the course of 10 hours. After this period a solution of 4.3 g (0.02 mol) of piperonylbromide in 30 cc of tetrahydrofuran is added dropwise to the mixture. The reaction mixture is stirred at 60° over the course of 8 hours, subsequently cooled to 20° 100 cc amounts of ether and water are added. The organic phase is separated off in a separating funnel, extracted with saturated sodium chloride solution, dried over sodium sulphate and evaporated. The residue may be purified by chromatography on silica gel with hexane/ethyl acetate (1:2). 2-Piperonylthio-ethanol is obtained as a colourless oil, which according to gas-chromatography is pure.

$n_D^{20} = 1.5883$

| Analysis: | $C_{10}H_{12}O_3S$ | | Molecular weight: 212.3 |
|---|---|---|---|
| Calc. | C 56.6 % | H 5.7 % | O 22.6 % S 15.1 % |
| Found | 56.3 % | 6.0 % | 23.0 % 15.6 % |

What is claimed is:

1. A compound of the formula

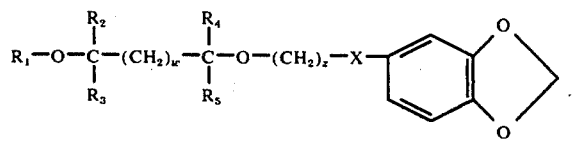

wherein $R_1$ is alkyl of 1 to 9 carbon atoms, alkenyl of 3 to 9 carbon atoms, alkynyl of 3 to 9 carbon atoms, cycloalkyl of 5 to 7 carbon atoms or cycloalkyl of 5 to 7 carbon atoms substituted by alkyl of 1 to 4 carbon atoms, $R_2$, $R_3$, $R_4$ and $R_5$ are independently hydrogen or alkyl of 1 to 4 carbon atoms, $w$ is 2 to 4, $z$ is 4 or 6, and X is oxygen, sulfur, —OCH$_2$— or —SCH$_2$—.

2. A compound of claim 1, wherein $R_1$ is alkyl of 1 to 9 carbon atoms.

3. A compound of claim 2, wherein one of $R_2$ and $R_3$, and, one of $R_4$ and $R_5$, is hydrogen.

4. A compound of claim 3, wherein X is oxygen or —OCH$_2$—.

5. A compound of claim 3, wherein X is —SCH$_2$—.

6. The compound of claim 4, which is [4-(4-isopentyloxy-butyloxy)-butyl]-piperonyl ether.

7. The compound of claim 4, which is [6-(4-isopentyloxy-butyloxy)-hexyl]-piperonyl ether.

8. The compound of claim 4, which is [6-(6-isopentyloxy-hexyloxy)-hexyl]-piperonyl ether, 9. A compound of claim 1, wherein $R_1$ is alkenyl of 3 to 9 carbon atoms.

10. The compound of claim 9, which is 6-[4-(5-allyloxy-2-hexyloxy)-butyloxy]-1,3-benzodioxol.

11. An insecticidal or acaricidal composition which comprises an insecticidal or acaricidal effective amount of a compound of claim 1 in association with an insecticide or acaricide carrier or diluent.

12. The composition of claim 11, further comprising a surfactant.

13. A method of combating insects or acarids in a locus, which comprises applying to the locus an insecticidally or acaricidally effective amount of a compound of claim 1.

* * * * *